United States Patent
Francescatti et al.

(10) Patent No.: US 7,726,318 B2
(45) Date of Patent: Jun. 1, 2010

(54) RADIATION BLOCKING PATCH FOR RADIO-THERAPY

(75) Inventors: Darius Francescatti, Barrington, IL (US); Michael Forman, Los Gatos, CA (US)

(73) Assignee: Xoft, Inc., Sunnyvale, CA (US)

( * ) Notice: Subject to any disclaimer, the term of this patent is extended or adjusted under 35 U.S.C. 154(b) by 483 days.

(21) Appl. No.: 11/385,255

(22) Filed: Mar. 20, 2006

(65) Prior Publication Data

US 2007/0016179 A1    Jan. 18, 2007

Related U.S. Application Data

(60) Provisional application No. 60/663,529, filed on Mar. 21, 2005.

(51) Int. Cl.
 *A61B 19/00* (2006.01)
 *A61N 5/00* (2006.01)
(52) U.S. Cl. .......................... 128/897; 600/3
(58) Field of Classification Search ............ 600/1, 600/2, 3, 7; 623/1.15, 1.42; 606/191, 151, 606/194; 514/44; 250/516.1; 128/898
 See application file for complete search history.

(56) References Cited

U.S. PATENT DOCUMENTS

| | | | |
|---|---|---|---|
| 3,872,856 A * | 3/1975 | Clayton | 600/6 |
| 5,045,708 A * | 9/1991 | Cooper | 250/519.1 |
| 5,090,043 A | 2/1992 | Parker et al. | |
| 5,153,900 A | 10/1992 | Nomikos et al. | |
| RE34,421 E | 10/1993 | Parker et al. | |
| 5,369,679 A | 11/1994 | Sliski et al. | |
| 5,422,687 A | 6/1995 | Tanaka et al. | |
| 5,422,926 A | 6/1995 | Smith et al. | |
| 5,452,720 A | 9/1995 | Smith et al. | |
| 5,528,652 A | 6/1996 | Smith et al. | |
| 5,566,221 A | 10/1996 | Smith et al. | |
| 6,033,357 A | 3/2000 | Ciezki et al. | |
| 6,059,713 A * | 5/2000 | Urick et al. | 600/3 |
| 6,066,856 A * | 5/2000 | Fishman | 250/519.1 |
| 6,077,213 A | 6/2000 | Ciezki et al. | |
| 6,309,339 B1 | 10/2001 | Ciezki et al. | |
| 6,350,226 B1 * | 2/2002 | Fischell et al. | 600/1 |
| 6,387,035 B1 | 5/2002 | Jung, Jr. et al. | |
| 6,409,651 B1 * | 6/2002 | Brown, III | 600/3 |
| 6,409,652 B1 * | 6/2002 | Kamdar et al. | 600/3 |
| 6,413,204 B1 * | 7/2002 | Winkler et al. | 600/3 |
| 6,464,626 B1 | 10/2002 | Peterson | |
| 6,482,142 B1 * | 11/2002 | Winkler et al. | 600/3 |
| 6,494,824 B1 * | 12/2002 | Apple et al. | 600/3 |
| 6,626,816 B1 | 9/2003 | Ciezki et al. | |
| 6,629,920 B2 * | 10/2003 | Liprie | 600/1 |
| 6,673,006 B2 * | 1/2004 | Winkler | 600/1 |
| 6,725,081 B2 | 4/2004 | Ciezki et al. | |
| 6,749,859 B2 * | 6/2004 | Leibowitz | 424/402 |
| 6,752,752 B2 * | 6/2004 | Geitz | 600/3 |
| 7,029,431 B2 * | 4/2006 | Apple et al. | 600/3 |

(Continued)

*Primary Examiner*—Samuel G Gilbert
(74) *Attorney, Agent, or Firm*—Thomas M. Freiburger

(57) ABSTRACT

A flexible, relatively flat and thin patch, optionally made of biodegradable material, substantially attenuates ionizing radiation from normal but sensitive anatomy during radiotherapy, particularly breast brachytherapy. The patch is of such a thickness as to substantially attenuate radiation by distance or consists of a material that has been formulated with radio-attenuating filler or is of radio-attenuating material. An alternative version consists of a thin patch that is coated with radio-attenuating material.

9 Claims, 3 Drawing Sheets

U.S. PATENT DOCUMENTS

| | | |
|---|---|---|
| 2004/0171740 A1 | 9/2004 | Ruberti et al. |
| 2005/0070753 A1 | 3/2005 | Forman et al. |
| 2006/0224034 A1* | 10/2006 | Reever .......................... 600/3 |
| 2007/0129592 A1 | 6/2007 | Lubock et al. |
| 2007/0167666 A1 | 7/2007 | Lubock et al. |
| 2007/0167667 A1 | 7/2007 | Lubock et al. |
| 2007/0191667 A1 | 8/2007 | Lubock et al. |
| 2007/0191668 A1 | 8/2007 | Lubock et al. |

* cited by examiner

RADIATION BLOCKING PATCH FOR RADIO-THERAPY

This application claims priority from provisional application Ser. No. 60/663,529 filed on Mar. 21, 2005.

BACKGROUND OF THE INVENTION

This invention concerns brachytherapy, particularly for treatment of surrounding tissue after removal of a malignant tumor. In particular the invention concerns protection of adjacent healthy tissue such as skin, bone or organs that would otherwise be susceptible to being overdosed with radiation.

Local radiation therapy is often prescribed following breast surgery. Traditionally, this radiation is supplied by large machines positioned over the patient in extensively shielded special radiation therapy rooms from which casual observers or therapists must be excluded during treatment. Breast brachytherapy is a more recently developed medical procedure that involves delivering ionizing radiation to breast tissue from inside of a surgical cavity formed after a lumpectomy procedure. Breast brachytherapy is typically performed with a balloon catheter or other type of applicator positioned inside the cavity. The balloon or applicator fills the cavity and provides a platform or channel for introduction of radioactive material or a miniature x-ray tube. It also serves to locate the radiation source within the cavity such that the ionizing radiation sterilizes accurately treats the margins of the surgical cavity. Radiation treatment of surgical margins has been shown to reduce the rate of recurrence of malignant tissue.

Preparatory to a breast lumpectomy, the tumor has usually been located by any of several means known to medical practitioners. During lumpectomy, it is common practice to excise not only the tumor, but also a margin around the tumor, often a centimeter radially, to assure all diseased tissue is removed. To commence a lumpectomy procedure, the surgeon sharply dissects breast tissue toward the tumor to be excised. As he gets close to the tumor, he starts to cut around the lesion until the target tissue has been separated from the surrounding, presumed normal tissue. At this point, the tumor and excised margin are removed through the incision, leaving a cavity within the breast.

Typically, pathology is determined after the surgery. A "clean" margin is a pathologic finding indicating there are no cancer cells at the resection margin. After assuring the margin surrounding the cavity is "clean", a course of radiotherapy is administered to reduce the likelihood of tumor recurrence. Brachytherapy is one modality of such radio-therapy and is of particular interest with this invention. During the brachytherapy treatment planning process, consideration is given to preventing collateral damage to radiation-sensitive structures closely adjacent to the tissue to be irradiated. Such structures may include bone, organs and skin. Where such structures are at risk, the preferred level of radiation therapy for diseased tissue is often moderated to prevent collateral damage, therefore lessening the therapeutic dosage which would otherwise preferably be delivered to target tissues surrounding the cavity.

In instances where such structures exist, and dose moderation is indicated, there is a need for local shielding or attenuation apparatus which can be applied within the cavity adjacent to the at-risk tissues in order effectively to moderate the dose selectively while not detracting from the preferred dosage delivered to diseased tissue elsewhere within the cavity. It is an object of this invention to provide convenient apparatus and methodology to locally moderate brachytherapy radiation.

SUMMARY OF THE INVENTION

Proxima Therapeutics (Alpharetta, Ga.) sells a breast brachytherapy device that consists of a balloon catheter or applicator with a channel formed by a polymer tube that runs through the long axis of the balloon. A radioactive isotope seed inside a probe or sleeve is placed inside the tube and pulled through the tube. Ionizing radiation is thus delivered to the tissue margins. This procedure is usually a fractionated treatment of, for example, 10 fractions over 5 days. At the completion of the treatment, the balloon is deflated and removed from the patient. The product is effective because it substantially reduces the overall time of radiation treatment compared to external beam radiation treatment for a breast cancer patient who has undergone a lumpectomy procedure. A large percentage of patients do not qualify for this treatment, however, because the surgical cavity lies in close proximity to the skin or other radiation sensitive structures within the anatomy. In this instance, the preferred dose of therapeutic radiation, if delivered, would be excessive with respect to the skin or adjacent structures, and would result in injury.

In one method used to commence the brachytherapy procedure, the physician introduces the applicator through a small incision made in the breast and into the surgical cavity. During introduction into the cavity, the balloon is deflated and has a small profile in order to traverse the small track leading into the cavity. When the balloon is inside of the cavity, it is inflated to a predetermined size tending to force the cavity to approximate the shape of the balloon. At that time, an image is taken showing the position of the surface of the balloon relative to the skin and other radiation sensitive structures. If there is less than a 5 mm distance, for example, between the surface of the balloon and the skin, the patient is disqualified from the treatment. The balloon is removed and the patient will then undergo an alternative form of radiation treatment.

The present invention provides a means of significantly increasing the number of patients who will qualify for optimal breast brachytherapy, reducing the approximately 30% of patients who are disqualified from this treatment when skin distance is postoperatively assessed and found to be prohibitive. This is accomplished by placement of a protective patch inside the cavity in direct apposition to the skin or other structure which would be injured by application of the preferred treatment if left unprotected. Alternatively, the patch can be placed postoperatively at the time of catheter insertion or as a separate procedure directly into the cavity. If desired, the patch may be held by suturing it to tissue.

The invention, then, consists of a single, flexible, polymer patch of an arbitrary, selected thickness which, in consideration of its radiation attenuating properties, is appropriate to reduce dosage received by at-risk tissue to an acceptable level when placed surgically inside the lumpectomy cavity in apposition to such at-risk structure. When the balloon is subsequently inserted into the cavity and inflated to form the tissue surface of the cavity, the patch serves to further distort the cavity, moving at-risk tissue away from the radiation source, thus protecting it. The patch can alternately be made of material that has been formulated with radio-attenuating filler such as barium so as to increase its attenuating properties, which can permit a thinner patch. As a further alternate construction, the patch can have a coating that contains radio opaque filler. The patch can be made of a biodegradable polymer material or of a non-biodegradable polymer material. It should be biocompatible in either event. The patch composition and dimensions may be chosen to completely shield underlying tissue at risk, or may be fashioned to merely moderate the incident radiation, as appropriate. "Moderate" as used in the claims is intended to refer to partial or complete shielding. Equivalent shielding effectiveness may result from a dense loading of radio-attenuating material in a thin patch, or may result from a thicker patch of more lightly or non-loaded material. The patch is flexible, preferably in sheet form, and preferably capable of being cut to desired size and shape.

In the case where the patch is made of a biodegradable material, the patch can remain in the cavity after the balloon has been removed. The patch will slowly degrade over time. Patent application Ser. No. 10/742,445Pub. No. 2005/0070753which pre-dates this disclosure, describes hydrogel materials that are biocompatible and do not generate acidic byproducts. Acidic byproducts are known to cause inflammation. One good hydrogel candidate is made of hyaluron. This material and others appropriate are listed in Pub. No. 2005/0070753and all of that disclosure is included in this application by reference. Collagen in a condition possessing appropriate structural integrity can also be used as a patch or pad.

Another version of the invention uses a non-biodegradable patch which may optionally comprise a radio-attenuating filler or coating. In this case, the patch preferably is tacky and placed over the area of the balloon that will be facing the skin or other radiation sensitive tissue. The patch preferably is elastic and thin and stretches with the balloon when inflated. When such a patch is affixed to the balloon by adhesion or other methods well known to those of skill in the art, the patch would be removed from the patient along with balloon removal at the completion of therapy. Silicone is a suitable material for this type of patch as is latex, nitrile rubber, Santoprene and other materials well known for use within the body that can be used for or in conjunction with fabrication of this device. Additional patch structures appropriate where only padding or spatial separation is desired might include woven or non-woven fabrics of either synthetic or natural materials. These include cotton gauze or any other fibrous material that is bio-compatible and practical in use, or channeled or zoned inflatable structures that remain generally flat (not bulbous) as they are inflated.

Another embodiment of the invention comprises coating a balloon with a radio-attenuating coating comprising a paint or curing emulsion that is placed onto a quadrant or segment of the balloon. The coated segment of the balloon can be rotated until the coated area is in apposition to the endangered tissue border. Treatment is thus delivered with the sensitive tissue protected. The apparatus is removed in the usual fashion.

With this invention, optimal prescribed doses of radiation may be delivered to diseased tissue, while adjacent structures elsewhere are easily protected. Although the description of this invention has been primarily with respect to breast brachytherapy, the inventive principles of the invention may also be applied to other techniques of radio-therapy and to other anatomy. These and other objects, advantages and features of the invention will be apparent from the following description of a preferred embodiment, considered along with the accompanying drawings.

DESCRIPTION OF PREFERRED EMBODIMENTS

Figure 1:
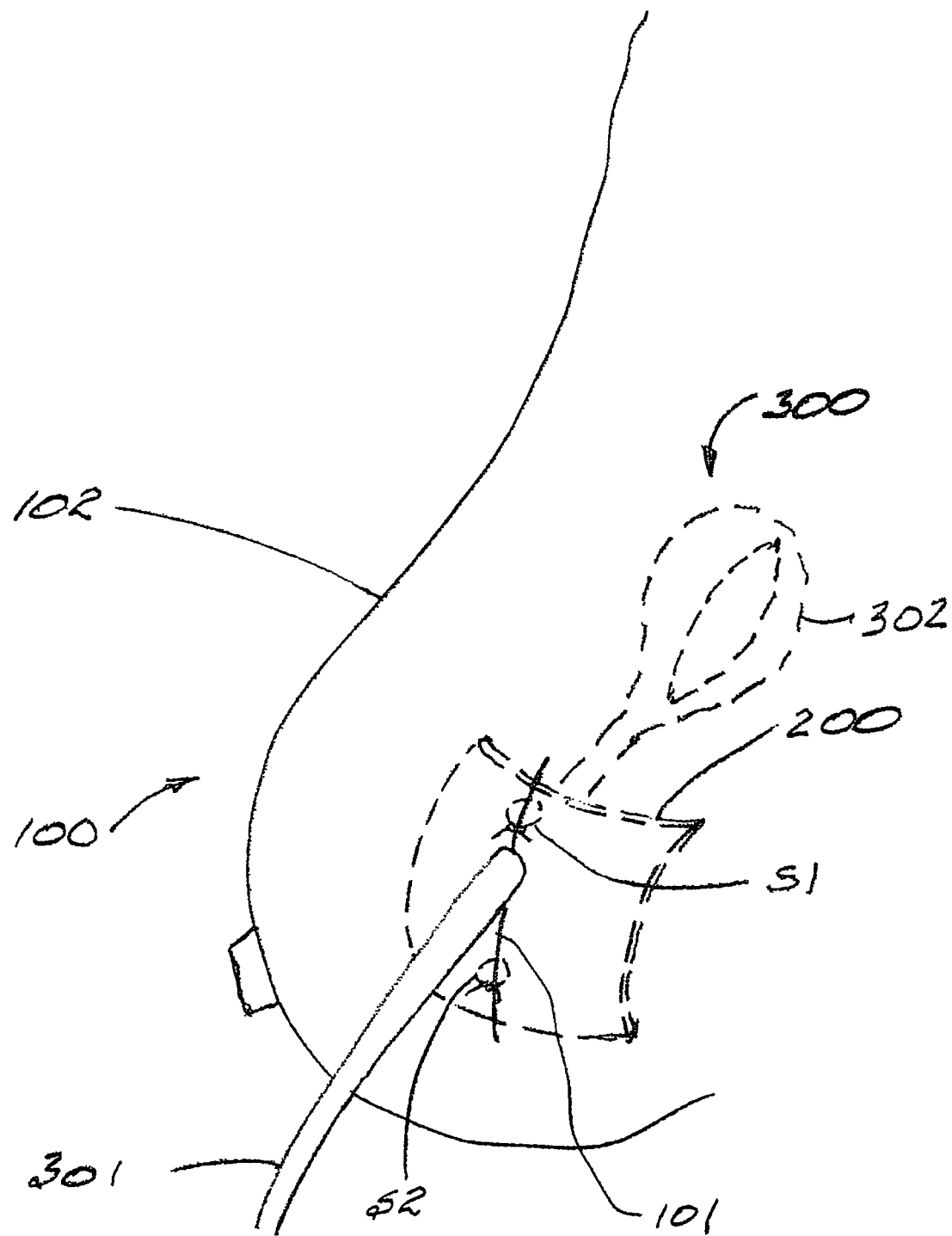
FIG. 1 is a perspective view showing a patch of the invention positioned under the skin of a breast and trimmed to accommodate the shaft of a catheter passing through the operative incision site and positioned within a cavity in the breast.
Figure 2A:
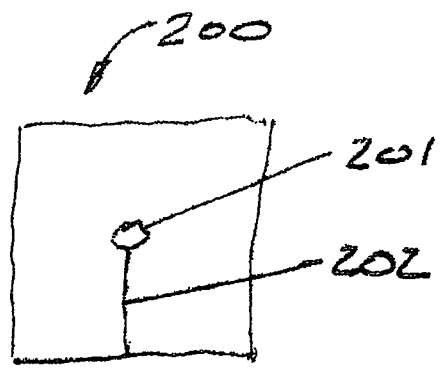
FIG. 2a shows in plan view a patch trimmed to accommodate the catheter shaft as shown in FIG. 1.

FIG. 1 shows a portion of a breast 100 with an incision 101 through which a shaft 301 of a catheter 300 is positioned. A balloon 302 is fixed to the distal end of the shaft. Under the skin 102 of the breast, a patch 200 is positioned. The patch 200 is trimmed as shown in FIG. 2a to accommodate assembly onto the catheter shaft 301. The patch is held in place by sutures S1 and S2.

FIG. 2a depicts a patch trimmed by forming a hole 201 for the shaft of the catheter, and a slit 202 such that the patch can be assembled onto the catheter shaft without recourse to the end of the catheter. Alternatively, the patch could be trimmed with the hole 201 only, and assembled over the end of the catheter 300 prior to placement in the breast.

Figure 2B:
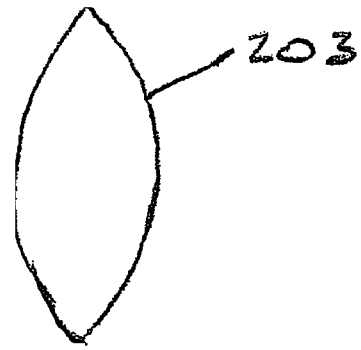
FIG. 2b shows in plan view a patch trimmed to lie on the surface of a quadrant of the balloon shown in FIG. 1.

FIG. 2b depicts a patch 203 trimmed to lie on a surface quadrant of the balloon 302 of the catheter 300 as shown in FIG. 1. It may be bonded onto the balloon with the balloon in either a deflated state on in an inflated state, as best suits the geometry of the situation and the properties of the balloon 302 and the patch 203. The patch may be self-adherent to the balloon, for example by a contact adhesive. It may also be secured to the balloon by other means well known to those of skill in the art, or placed directly on breast tissue within the cavity, and optionally secured in place.

Figure 3:
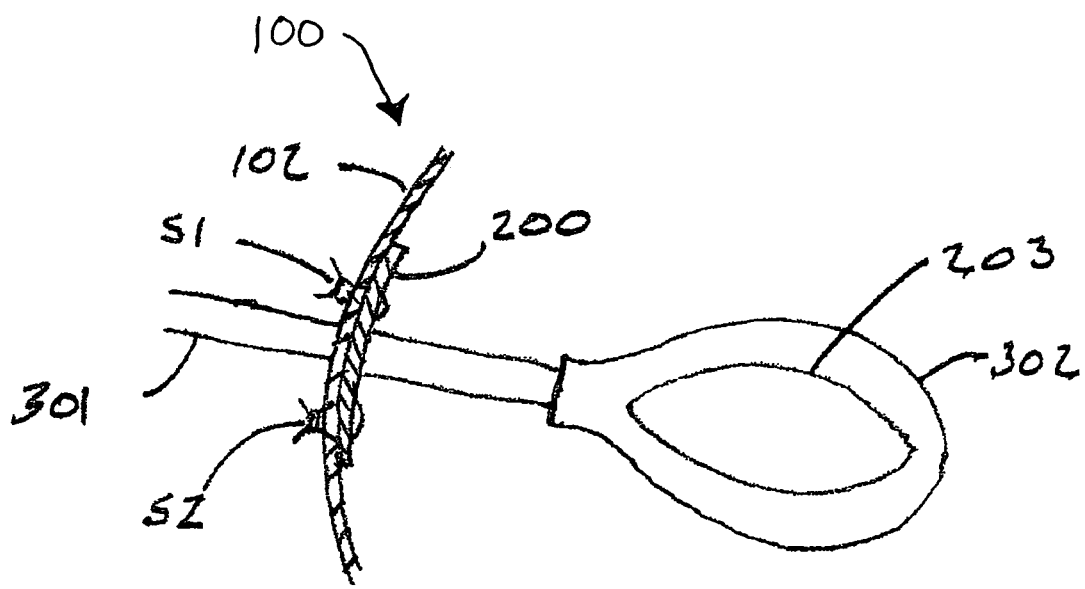
FIG. 3 shows in cross section through the skin of the breast, the skin patch, the skin and the shaft of the catheter shown in FIG. 1.

FIG. 3 depicts a cross section view through the breast 100 at the entry of the catheter shaft 301 through the skin 102 of the breast, and through the patch 200, and the catheter balloon in place within the breast cavity. The balloon is shown inflated, and has positioned on a quadrant of it, a second patch 203 such as shown in FIG. 2b, placed so as to protect an internal anatomical structure, for example, a bone. The patch at the incision site is shown held in place by sutures S1 and S2, as again depicted in FIG. 1.

Figure 4:
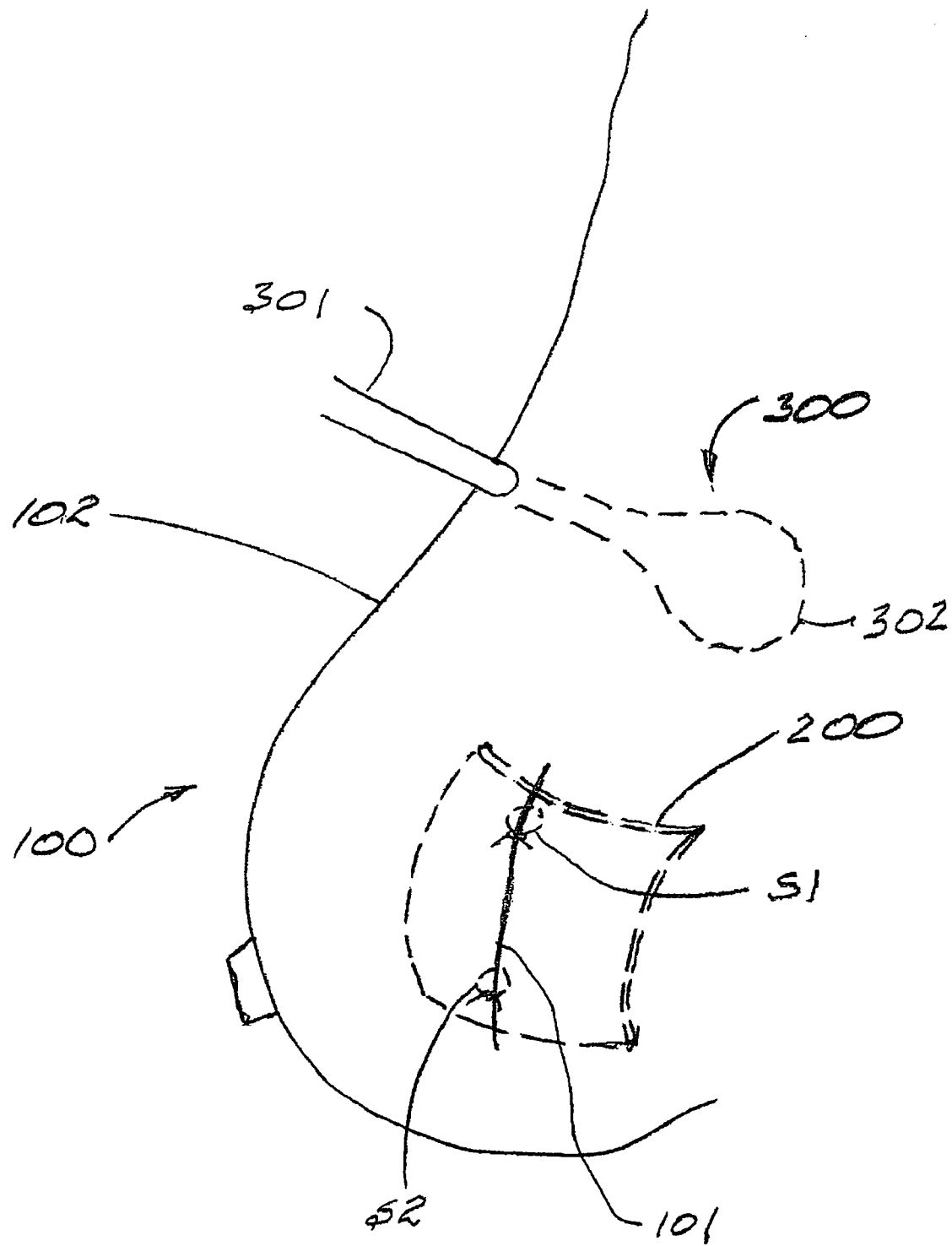
FIG. 4 is a perspective view showing a patch of the invention positioned under the skin of a breast at the incision site with the catheter entering and passing through breast tissue at a site other than the operative incision site, and positioned within a cavity in the breast.

FIG. 4 shows a portion of a breast 100 with an incision 101. Under the skin 102 of the breast, a patch 200 is positioned, generally as shown in FIG. 1. If necessary, the patch 200 may be trimmed to accommodate the patient's anatomy. The patch is held in place by sutures S1 and S2. The catheter 300 has been introduced through the skin 102 of the breast at a different location and advanced into the breast 100 into a cavity from which the brachytherapy will be performed.

In using the patch of the invention, the surgeon first completes his lumpectomy. The surgeon then examines the cavity and locates anatomical tissue and structure which should be shielded, or partially shielded during brachytherapy treatment. The surgeon then determines how best to optimally shield the at-risk structures and prescribes patch style, size and placement, as well as how to place and secure the patch or patches within the cavity or on the surface of the balloon 302. If a subcutaneous patch is to be employed, the patch is affixed intra- or post-operatively where indicated in order to protect the skin. With this invention, the therapist is able to deliver optimal therapeutic doses of radiation to target tissues surrounding the excision cavity while protecting normal, at risk tissues and structures.

Another embodiment of the method of this invention primarily relies on spatial separation for attenuating of radiation on at-risk tissue. If, in the postoperative assessment of the patient, it is determined that critical distances between the radiation source and at-risk structures are lacking, a radiation moderating (optionally blocking) patch can be shaped and affixed to tissue or to a portion of the balloon on the applicator as shown in FIG. 3 prior to insertion into the cavity. Before radiation therapy commences, the balloon must be carefully positioned such that the patch is placed in apposition to the at-risk tissue.

While this invention has been described in terms of certain preferred embodiments, other embodiments can be readily devised by those of skill in the art in view of the teachings above.

Accordingly, the scope of the present invention should not be limited by the foregoing discussion, but should rather be defined by reference to the claims which follow.

What is claimed is:

1. A method of delivering differentiated doses of ionizing radiation to adjacent regions of patient anatomy during brachytherapy performed with an applicator positioned within a cavity of the patient, comprising:
    providing a set of flexible generally sheet-like spacer devices having a series of different thicknesses,
    selecting from the set of spacer devices having a series of different thicknesses, a spacer device of desired thickness, the spacer device being a substantially flexible structure which is biocompatible,
    placing the selected spacer device so as to be positioned between the applicator containing a radiation source and an area of patient anatomy, within the cavity of the patient's tissue, and
    irradiating the patient's tissue using the radiation source, with the spacer device holding said area of patient anatomy at a desired spacing away from the applicator and thus away from the radiation source, such that radiation received by said area of patient anatomy is attenuated by increased distance from the source.

2. The method of claim 1, including making an incision in the patient's skin and adjacent tissue, and wherein the spacer device is placed subcutaneously within the incision.

3. The method of claim 1, wherein the brachytherapy applicator comprises a balloon positioned within the surgical cavity from which the brachytherapy will be applied.

4. The method of claim 1, wherein the spacer device is positioned within a surgical brachytherapy cavity and affixed directly to a region of tissue surrounding the cavity, said region of tissue being said area of patient anatomy.

5. The method of claim 4, wherein the spacer device is affixed to said region of tissue by suturing.

6. A radiation attenuating device for use in conjunction with ionizing radiation therapy, comprising:
    a set of flexible generally sheetlike spacer structures having a series of different thicknesses,
    each of the set of spacer structures being biocompatible, for use inside a human patient.

7. The apparatus of claim 6, wherein the set of flexible generally sheet-like spacer structures includes spacer structures of varying length or width, as well as thickness.

8. The apparatus of claim 6, wherein each of the flexible generally sheetlike spacer structures has the ability to be manually shaped to a desired size and configuration.

9. The apparatus of claim 6, wherein the flexible generally sheet-like spacer structures are bio-absorbable.

* * * * *